US008425429B2

(12) United States Patent
Tommerdahl et al.

(10) Patent No.: US 8,425,429 B2
(45) Date of Patent: Apr. 23, 2013

(54) DEVICES, SYSTEMS AND METHODS FOR VIBROTACTILE STIMULATION AND NON-INVASIVE NEUROLOGICAL SCREENING

(75) Inventors: Mark Allen Tommerdahl, Chapel Hill, NC (US); Robert Glenn Dennis, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 839 days.

(21) Appl. No.: 12/302,731

(22) PCT Filed: May 29, 2007

(86) PCT No.: PCT/US2007/012620

§ 371 (c)(1), (2), (4) Date: Jun. 18, 2009

(87) PCT Pub. No.: WO2007/139996

PCT Pub. Date: Dec. 6, 2007

(65) Prior Publication Data

US 2009/0270775 A1 Oct. 29, 2009

Related U.S. Application Data

(60) Provisional application No. 60/808,923, filed on May 26, 2006.

(51) Int. Cl.
*A61B 5/00* (2006.01)

(52) U.S. Cl.
USPC .......................................... 600/552; 600/300

(58) Field of Classification Search .................. 600/552, 600/300, 306, 557; 601/46, 48, 60, 67, 69–71, 601/78, 79, 82
See application file for complete search history.

(56) References Cited

U.S. PATENT DOCUMENTS

| | | | |
|---|---|---|---|
| 5,022,407 | A | 6/1991 | Horch et al. |
| 5,381,805 | A | 1/1995 | Tuckett et al. |
| 5,611,771 | A | 3/1997 | Taylor |
| 6,326,901 | B1 | 12/2001 | Gonzales |

OTHER PUBLICATIONS

International Search Report and Notification Concerning availability of the publication of the international application for PCT Application No. PCT/US2007/012620 dated May 26, 2006.

*Primary Examiner* — Kristen Matter
(74) *Attorney, Agent, or Firm* — Olive Law Group, PLLC

(57) ABSTRACT

Devices, systems, methods, and computer program products are disclosed for non-invasive diagnosis and screening of neurological disorders. Spatio-temporal mapping can be utilized between the skin and the central nervous system to rapidly, painlessly and quantitatively assess functional connectivity in the central nervous system. Stimulation drivers can be independently operated to control the movement of stimulators to achieve a variety of desired stimulation parameters.

22 Claims, 13 Drawing Sheets

DEVICES, SYSTEMS AND METHODS FOR VIBROTACTILE STIMULATION AND NON-INVASIVE NEUROLOGICAL SCREENING

RELATED APPLICATIONS

This application is a 35 U.S.C. 371 national stage application of PCT Application No. US2007/012620, filed May 29, 2007, and claims the benefit of U.S. Provisional Patent Application Ser. No. 60/808,923, filed May 26, 2006. The disclosure of U.S. Provisional Patent Application Ser. No. 60/808,923 is incorporated herein by reference in its entirety.

GOVERNMENT INTEREST

This invention was made with U.S Government support under the National Institutes of Health RO1 grant NS043375. The U.S. Government has certain rights in the invention.

TECHNICAL FIELD

The present subject matter generally relates to non-invasive analysis of human cortical-cortical interactions. More particularly, the present subject matter relates to devices, systems, methods, and computer program products for vibrotactile stimulation and neurological screening by analysis of cortical-cortical interactions and comparisons to normal cortical function.

BACKGROUND

One of the intriguing questions in the field of systems neuroscience is the impact that cortical-cortical interactions have on a how a subject perceives and discriminates various sensory stimuli. A number of neurological diseases have been found, or have been predicted to be, the result of abnormal connectivity between different regions of the brain. These neurological diseases include, but are not limited to autism, schizophrenia, Alzheimer's and attention deficit and hyperactivity disorder (ADHD). Despite the knowledge of this correlation, the functional connectivity between brain regions is quite difficult to study, and most studies currently employ methods that are not only high in cost (such as fMRI), but also in the amount of time that it takes to make the observations necessary to gain insight into the interactions that take place between different cortical regions.

It would therefore be advantageous to provide devices and methods for performing diagnostic tests that can directly and non-invasively measure cortical-cortical interactions of a subject and also provide devices that can rapidly, painlessly and quantitatively assess functional connectivity in the central nervous system.

SUMMARY

In accordance with this disclosure, devices, systems, methods, and computer program products for vibrotactile stimulation and neurological screening are provided. It is, therefore, an object of the present disclosure to provide devices, systems, methods, and computer program products for performing diagnostic tests that can directly and non-invasively measure cortical-cortical interactions of a subject. Another object of the present disclosure is to provide devices, systems, methods, and computer program products that can rapidly, painlessly and quantitatively be used to assess functional connectivity in the central nervous system. These and other objects as can become apparent from the present disclosure are achieved, at least in whole or in part, by the subject matter described herein.

The subject matter described herein can be implemented as a computer program product comprising computer executable instructions embodied in a computer readable medium. Exemplary computer readable media suitable for implementing the subject matter described herein can include disk memory devices, chip memory devices, application specific integrated circuits, programmable logic devices, downloadable electrical signals, and/or any other suitable computer readable media. In addition, a computer program product that implements the subject matter described herein may be located on a single device or computing platform. Alternatively, the subject matter described herein can be implemented on a computer program product that is distributed across multiple devices or computing platforms.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which.

DETAILED DESCRIPTION

Figure 1:
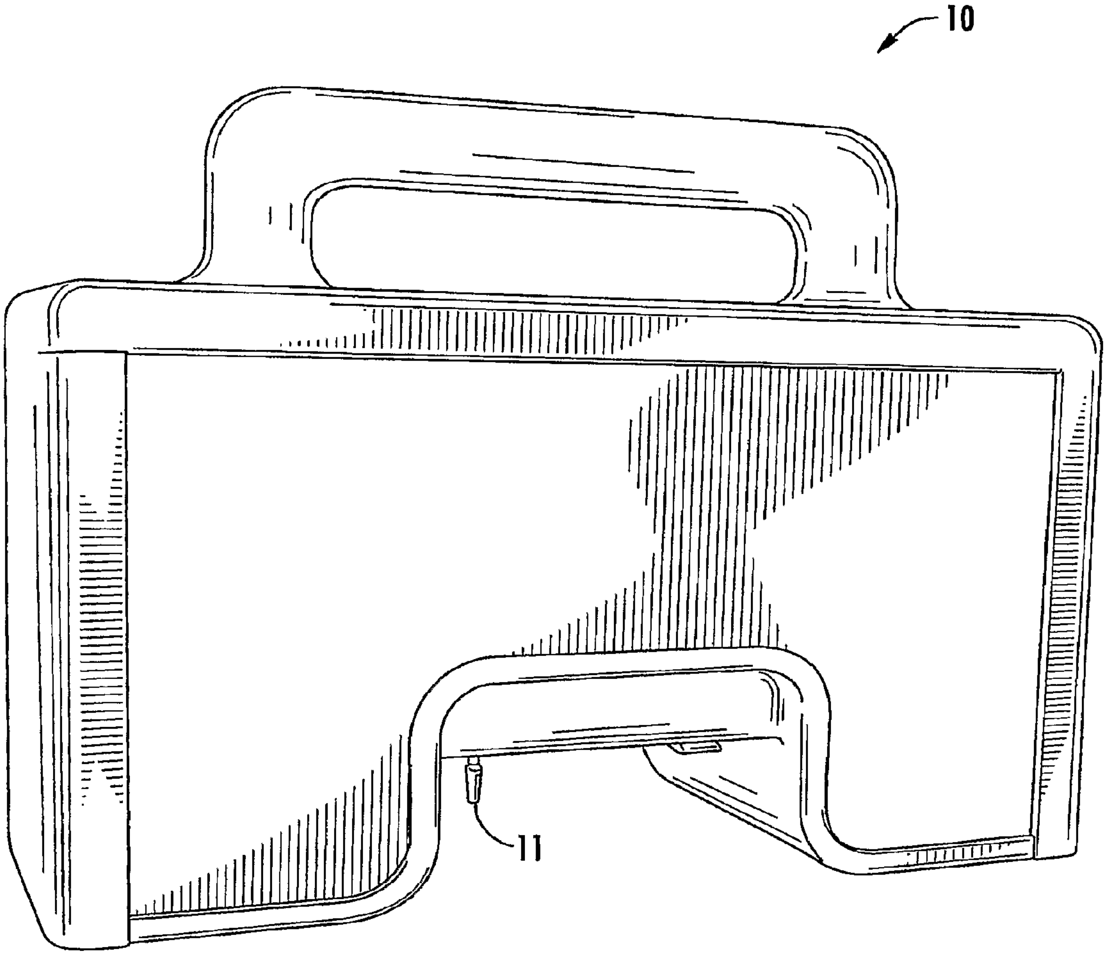
FIG. 1 is a perspective view of an embodiment of a device according to the present subject matter.

Reference will now be made in detail to possible embodiments of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

It has been shown that direct and noninvasive testing can demonstrate a high degree of correlation between changes in sensory perception and the response predicted by cortical data obtained from a number of animal studies. For example, simple neurological measures can be used to assess differences from normal cortical function. One such neurological measure, referred to as "two-point discrimination," involves the observation that when two points are placed closely on the skin, they can feel as though they are one point. At some point in time, the two points can be perceived as two-points as they are moved farther apart. It has further been shown that the response of a test subject exhibiting normal cortical-cortical interactions to two-point discrimination can improve under some conditions of vibrotactile stimulation and be made worse in other conditions. These findings indicate that the cortical-cortical interactions observed in a normal sensory cortex play a major role in sensory perception.

Subjects having neurological diseases, disorders, or disruptions such as autism, schizophrenia, Alzheimer's, ADHD, chronic pain, traumatic brain injury (TBI), and migraine, however, exhibit altered cortical functionality that can be detected with dynamic sensory testing. In particular, the fundamental building blocks necessary for normal cortical information processing in some neurological disorders or neurological states can be altered in such a way as to limit the functional connectivity within and between the fundamental components of cortical circuitry.

Generally, the integration of information from two closely spaced stimuli depends on the integration of both spatial and temporal information. It has been found according to the present subject matter, however, that in individuals having certain neurological disorders such as those noted above, this integration of information does not occur properly. In such subjects, there is a significant measurable difference between the observations obtained from these subjects and control subjects. As a result, the devices, systems, methods, and computer program products disclosed herein can be used to study not only neurological disorders such as those noted above, but can also be used to evaluate the efficacy of therapies (pharmacological or otherwise) on subjects afflicted with disorders as a diagnostic screening tool for the early detection of a wide variety of neurological disorders and/or to track the progression of any centrally mediated neurological disorder.

The devices, systems, methods, and computer program products disclosed herein can also be used in conjunction with other tests and treatments. For example, by adding the diagnostic methods disclosed to a patient's other physical and neurological tests, the decision to return an athlete to competition or a soldier to active duty after mild or traumatic brain injury (MBI or TBI) could be made with greater confidence and with less risk of re-injury. Diagnostic evaluations of treatments administered to TBI patients can also be improved with the additional information provided by these metrics.

The information provided by these devices, systems, methods, and computer program products can lead to more effective diagnostic and therapeutic strategies for the as many as 1 in 166 births that result in a child with autism. Applications of these methods to other central nervous system (CNS) disorders may prove beneficial as well.

The disclosed subject matter can help with the establishment of baseline biomarkers of aging. In this way, primary health care workers can be given a method that would aid in the early diagnosis and possible intervention in subjects with Alzheimer's. Though statistics range significantly in the literature, Alzheimer's has been claimed to affect as high as 50% of the population by the age of 85.

Chronic pain is highly prevalent in the geriatric population and at present there are few tools and procedures that enable healthcare providers to make informed decisions regarding the diagnosis and treatment choices for a variety of chronic pain conditions. The disclosed devices, systems, methods, and computer program products provide such a tool.

The disclosed subject matter can also aid in the development of novel pharmaceuticals that may benefit individuals in professions that operate on minimal sleep. Additionally, data from this research area can allow diagnostics in other clinical areas to be more accurate if baseline effects of sleep deprivation and/or fatigue can be accounted for.

Quantitative metrics generated by the diagnostic system can aid health care providers with a means to assess the impact of drug administration on the CNS. Current collaborative studies aim to assess the efficacy of drugs used for the treatment of chronic alcohol abuse.

With the establishment of baseline values from a significant database, cortical metrics obtained from individual patients can aid health care providers to objectively diagnose the general cortical health of a patient. It is anticipated that cerebral cortical health could be assessed in a manner similar to the way that blood pressure is used to assess the health of the heart and circulatory system. Measures outside the normal range for a patient demographic (age, gender, ethnicity, etc.) could provide guidelines to further diagnosis and possible intervention Accordingly, in one aspect, the disclosed subject matter provides devices, systems, methods, and computer program products for obtaining objective measures for how well cortical regions that are spaced at varying distances interact with one another. To date, observations obtained have involved interactions that take place between cortical areas that are activated by different types of skin stimulation. (It should be noted that, in general, all of the cortex develops in the same way and is organized in a similar fashion, and developmental and degeneration problems often affect all parts of the cortex similarly.) Closely aligned cortical regions can be activated by stimulating regions of the skin that are very close; cortical regions that are far away from each other may be activated by stimulating skin sites that are either remote to one another (such as stimulating skin sites on opposite hands) or by stimulating skin sites with stimuli of varying modality that activate very different cortical areas.

Referring to FIG. 1, one example of a vibrotactile stimulation device generally designated 10 is provided for the direct and noninvasive diagnostic testing of cortical-cortical interactions through vibrotactile stimulation. Stimulators 11 can extend from vibrotactile stimulation device 10 for providing vibrotactile stimulation to a test subject as part of a diagnostic test procedure. In this regard, a test subject can be positioned beneath the free ends of stimulators 11, which can be positioned in near contact with the test subject. Stimulators 11 can be driven to apply a stimulus to the test subject, where the subject's response to the stimulus can be recorded and compared to known response patterns.

Figure 2A:
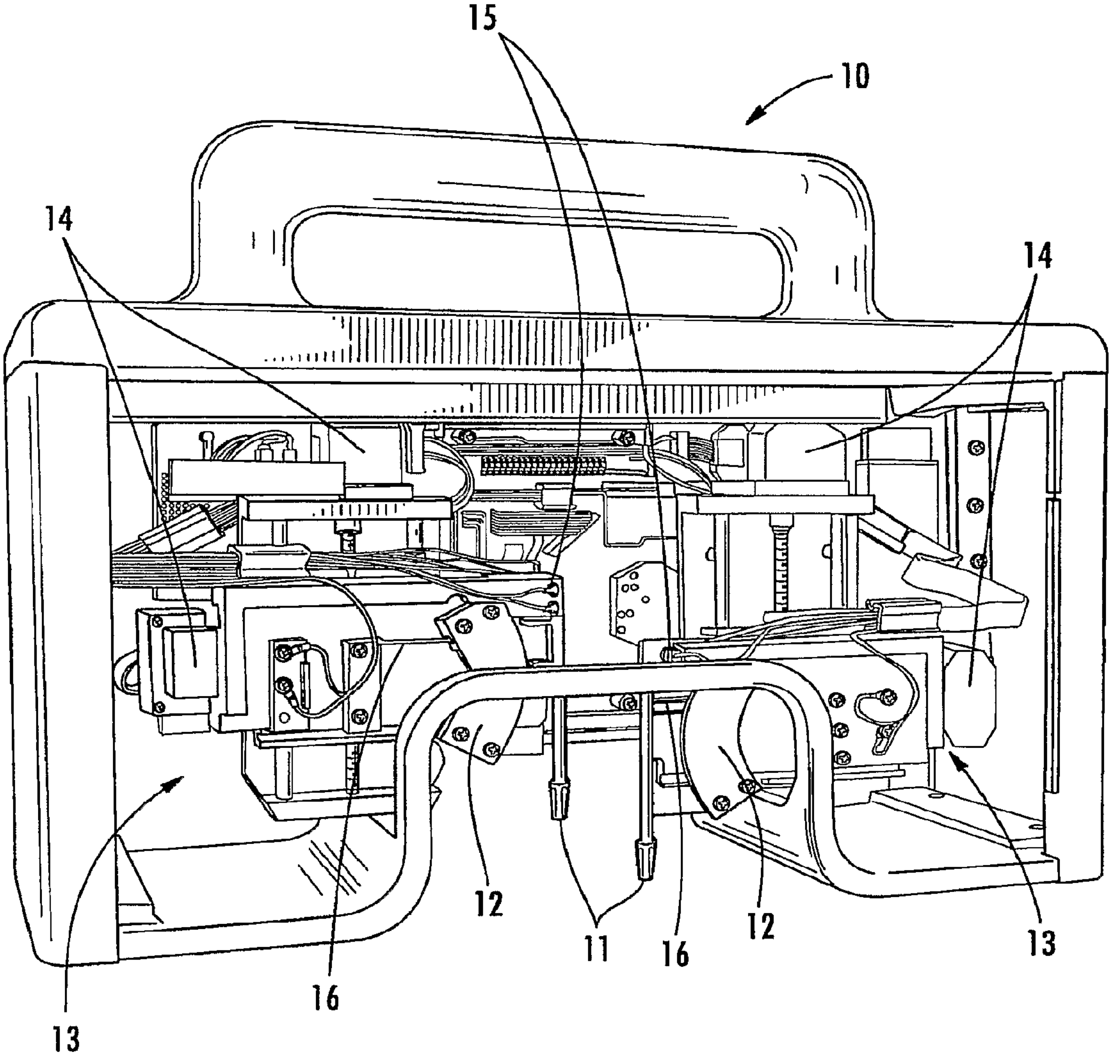
FIG. 2A is a perspective front view of the device of FIG. 1 showing internal components.

As shown in FIG. 2A, stimulation drivers 12 of vibrotactile stimulation device 10 can be operatively coupled to stimulators 11 to drive the local movement of stimulators 11. For example, stimulation drivers 12 can be vibration generators provided as voice coil actuators (VCAs) or other suitable mechanisms that can respond to electric signals to precisely control the movement of stimulators 11. The VCA stimulation drivers 12 can then be coupled to stimulators 11 by linkage 16 (e.g., four-bar linkage) to translate the motion of the VCA to vertical oscillation of stimulators 11. Stimulation drivers 12 can be independently operated to control the movement of stimulators 11 to achieve stimulation parameters such as, without limitation, the amplitude of oscillation, frequency of oscillation, phase relationship of multiple stimulators 11, onset time, duration of stimulation, vertical displacement of each stimulator 11 (e.g., at least 2 mm), lateral displacement of each stimulator 11, and force offset. For example, the stimulation drivers 12 can be provided such that they are capable of driving each stimulator 11 from DC to at least 200

Hz, with displacements of at least 2 mm (at DC) to at least 100 microns (at 200 Hz). A waveform generator (e.g., DAC) can be used to provide a sinusoidal signal to the stimulation drivers 12. The waveform generator can be provided as a separate component in communication with the vibrotactile stimulation device 10, or it may be integrated within the vibrotactile stimulation device 10.

Stimulation drivers 12 can be independently controlled, but the operation of stimulation drivers 12 can still be coordinated. In this regard, oscillations of stimulators 11 can occur and be driven while maintaining spatial and temporal relationships between stimulators 11. Despite this coordination, stimulation drivers 12 can still be capable of independent and spatio-temporally coupled control of respective stimulators 11 in terms of vibration/oscillation.

Figure 2B:
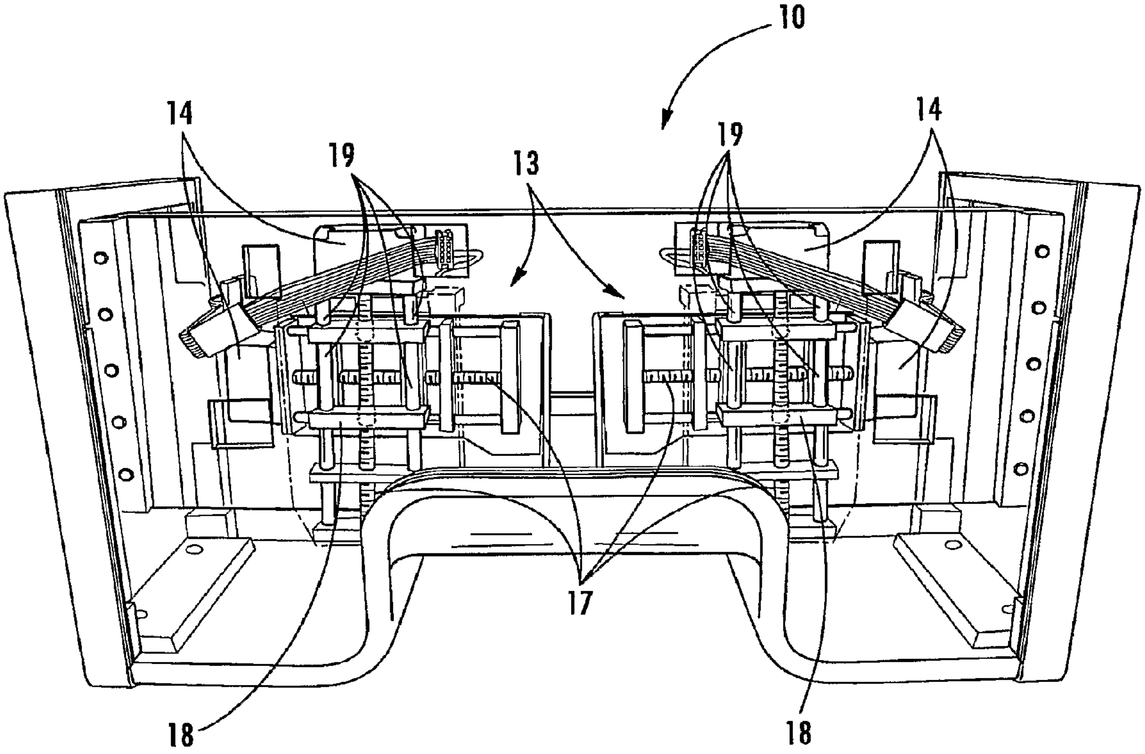
FIG. 2B is a perspective, rear view of the device of FIG. 1 with some internal component removed.

As depicted in FIGS. 2A and 2B, independent positioning systems 13 can be provided to drive larger-scale movement of each of stimulators 11. In the illustrated embodiment, motors 14 power the movement of positioning systems 13 associated with each of stimulators 11. In this way, the vertical position of stimulators 11 can be adjusted to accommodate different sizes of test subjects positioned beneath the tips of stimulators 11. Additionally, positioning systems 13 can be used to adjust the horizontal position of stimulators 11, changing the separation between the tips of stimulators 11.

For instance, in one embodiment, positioning systems 13 can each include a pair of stepper motors 14 coupled to power screws for operating an x-y table (i.e., motors 14 driving the rotation of power screws 17 such that traveler block 18 translates along guide rails 19). One stepper motor can be for driving movement of each stimulator 11 in a horizontal (i.e., lateral) direction, and the other stepper motor can be for driving vertical movement. In this manner, stimulators 11 can be raised or lowered to the desired position and the horizontal spacing between stimulators 11 can be adjusted from zero (i.e., stimulators touching) to a maximum separation (e.g., 30 mm each from center, 60 mm total).

In conjunction with positioning system 13, stimulation drivers 12 can further be used not only to drive the oscillation of stimulators II, but to detect contact with the test subject and/or the force of such contact. In this way, stimulation drivers 12 can provide feedback to the positioning system 13 during initial vertical positioning of the stimulators 11 to help set the stimulators 11 at or near the test subject. For instance, the stimulator position at which the stimulation drivers 12 register a 0.1-0.2 g change in resistive force can be interpreted as the point at which the stimulator 11 makes initial contact with the test subject.

In this arrangement, vibrotactile stimulation device 10 can be used for precise positioning and operation of stimulators 11 in a variety of positions for the administration of a wide range of somatosensory testing. FIGS. 3A through 3D illustrate some of the many configurations possible through the operation of positioning systems 13 and stimulation drivers 12. For example, stimulators 11 can be operated one at a time (see FIG. 3B) or simultaneously at a variety of positions (e.g., stimulators relatively close to each other in FIG. 3C, and spaced more apart in FIG. 3D).

Position sensors 15 can also be provided to monitor the vertical position of stimulators 11. Position sensors 15 can be integrated with a proportional integral derivative (PID) control system to monitor and correct the displacement of stimulators 11 to ensure the oscillations of stimulators 11 are in accordance with the desired parameters. Position sensors 15 that cause low levels of drag and/or hysteresis on the movement of stimulators 11, such as an optical sensor, can promote the efficient operation of vibrotactile stimulation device 10.

Figure 2C:
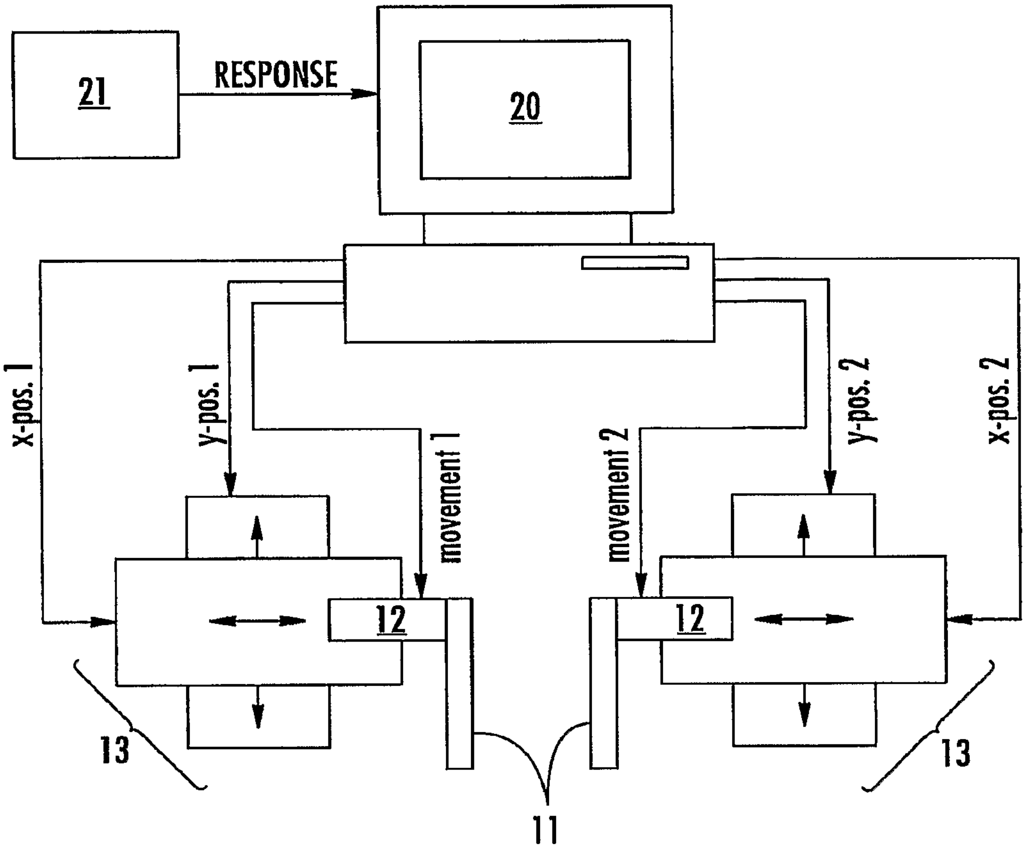
FIG. 2C is a schematic view of the device of FIG. 1.
Figure 3A:
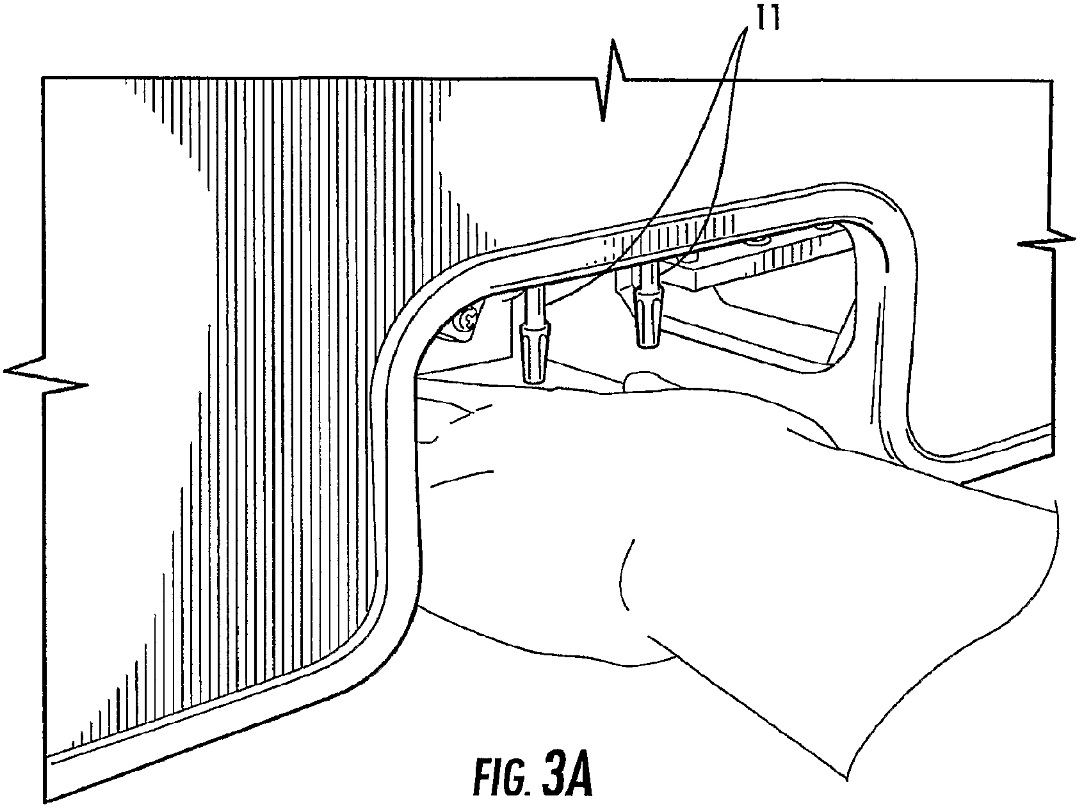
FIGS. 3A-3D are partial perspective views of a device according to the present subject matter in various testing positions.
Figure 3B:
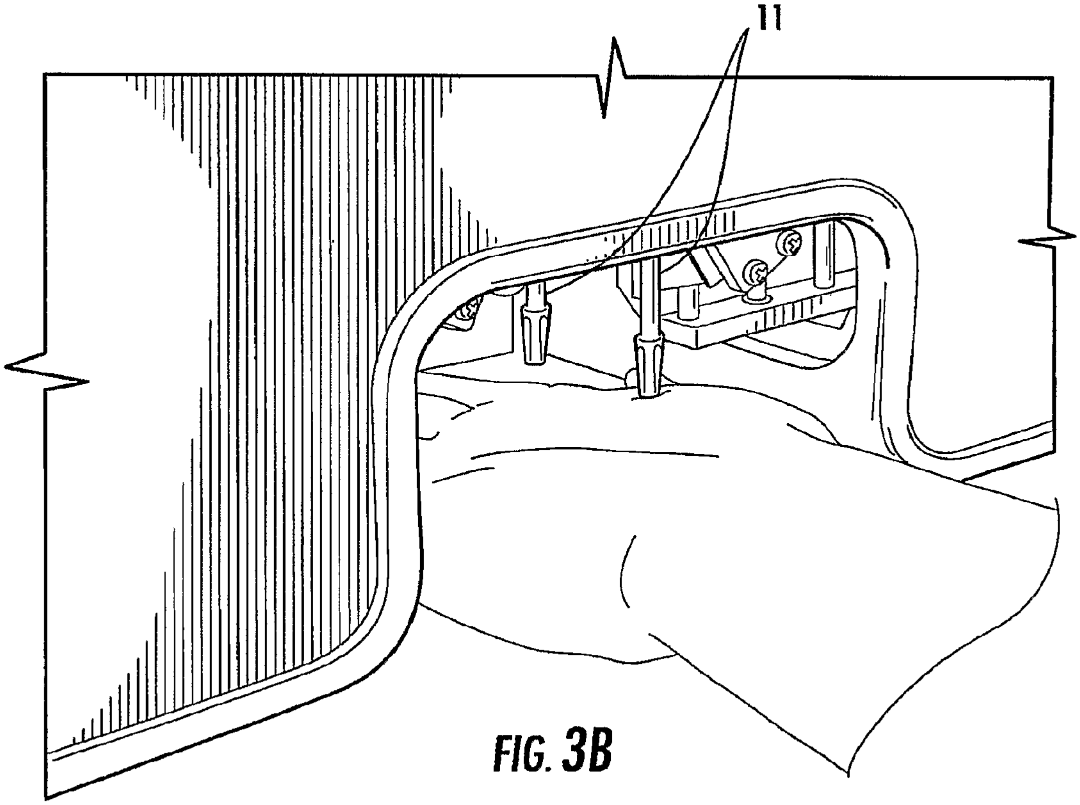
Figure 3C:
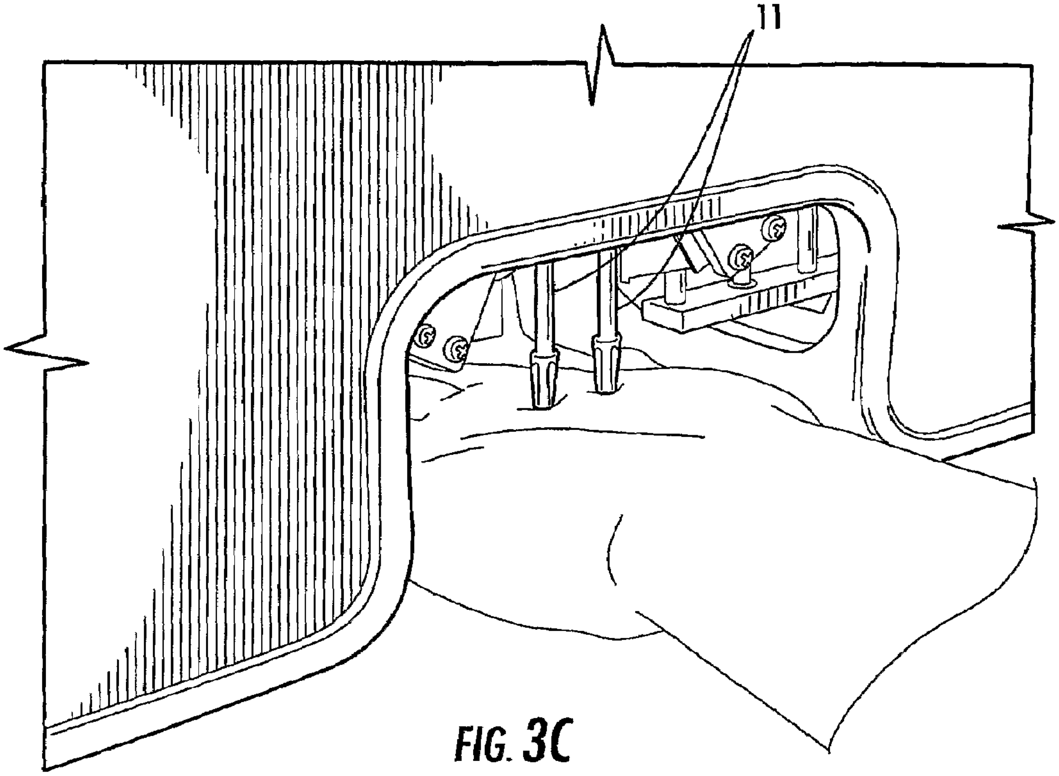
Figure 3D:
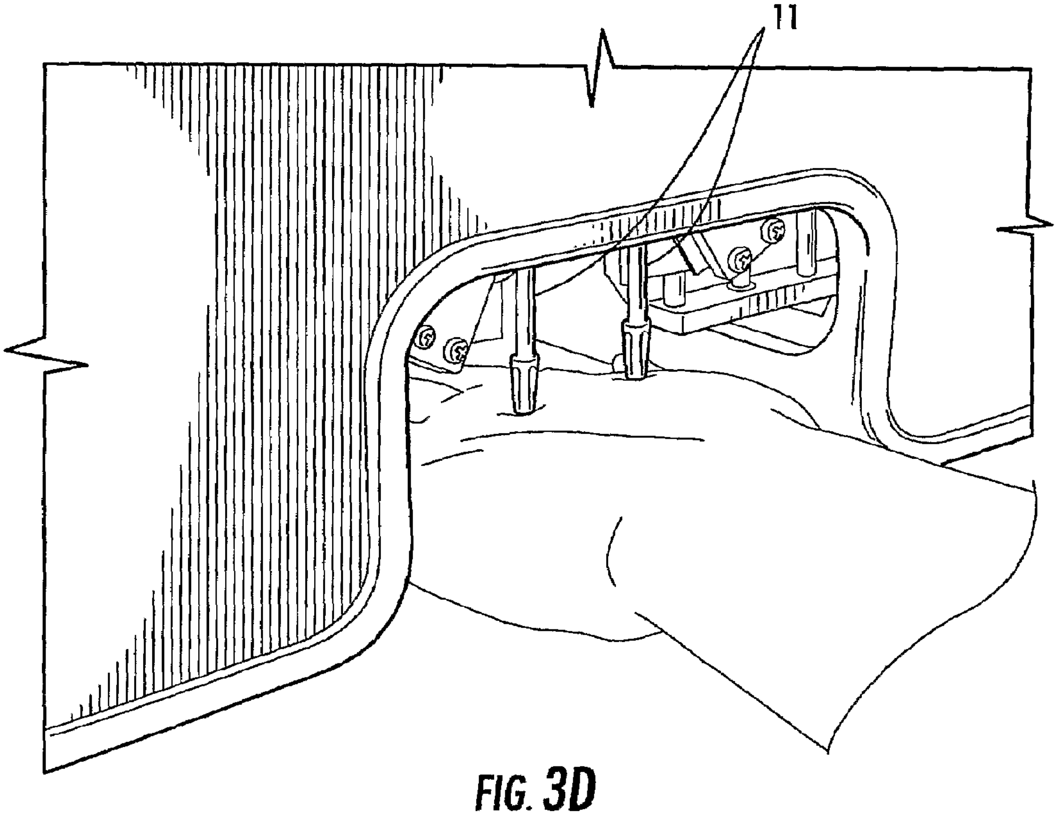

Referring to FIG. 2C, microprocessor 20 can be incorporated, either within vibrotactile stimulation device 10 or connected externally (e.g., via USB), to provide inputs to the control devices of vibrotactile stimulation device 10. Such inputs can include the horizontal position (i.e., x-position) and vertical position (i.e., y-position) to each of positioning systems 13, or the stimulation parameters (e.g., amplitude, frequency, phase relationship) to stimulation drivers 12. A response signal generator 21 can transmit a response to the stimuli from the test subject to microprocessor 20, which can be used to assess the cortical function of the test subject. Examples of response signal generator 21 can include a push button, foot pedal, or means for computer recognition of the test subject's vocal response to the stimuli.

The sensory testing provided by vibrotactile stimulation device 10 can enable the objective evaluation of the elaborate neuroanatomical connectivity that sub-serves the neuronal communication between adjacent and near-adjacent regions within sensory cortex that is widely recognized to be essential to normal sensory function. Although this intra-cortical communication can involve numerous mechanisms, diagnostic testing using vibrotactile stimulation device 10 can be specifically sensitive to the status of mechanisms currently believed by many to play major roles in the disorders of sensory cortical information processing that all too frequently compromise quality of life in a number of neurologically compromised individuals (i.e., neurotransmission mediated by the inhibitory neurotransmitter gamma aminobutyric acid (GABA) and by N-methyl-d-aspartate (NMDA) receptors, and interactions/interdependencies between neurons and glial cells).

In one particular embodiment, vibrotactile stimulation device 10 can employ embedded control of two separate, miniaturized vibratory coils controlled by embedded, micro-power microcontrollers with high-current output drive circuitry and an embedded USB interface to a laptop using the Microchip PIC18LF4550 microcontroller family. At least two separate stimulators 11 that can be spatially separated from 0.5 to 60 mm on an X-Y grid can be controlled with identical and/or different amplitudes and frequencies with selectable phases. Stimulators 11 can deliver vibrotactile stimuli in the range of 0 to 300 microns peak to peak amplitude at frequencies in the range from 1 to 300 Hz. The entire system can further be mounted on a lightweight system that is mounted or otherwise coupled (e.g., Velcro straps) on the subject's forearm.

Stimulators 11 can include additional functionality to enable an even broader range of sensory testing. For instance, the tips of stimulators 11 in contact with the test subject can be temperature variable to introduce an additional character to the applied stimulus, or the size of the tips of stimulators 11 can be varied to alter the sensory stimulus. Further, stimulation drivers 12 can provide not only a vertical oscillation but also a lateral stimulus, again altering the applied stimuli to broaden the range of sensory testing.

Use of vibrotactile stimulation device 10 described above allows for the initiation of a large scale study of the dynamic sensory discriminative deficits that undoubtedly occur in a population of subjects that utilizes cortical strategies that are very different from the normal subject population. Additionally, the detection of pharmacological effects is also possible and provides researchers studying neurological disorders with an effective means for objectively measuring the effect that administered drugs have on the cortical information processing capabilities of a subject.

Accordingly, in another aspect, the disclosed subject matter provides devices, systems, methods, and computer program products for performing diagnostic tests that can directly and non-invasively measure the cortical-cortical interactions of a subject. Briefly, it is believed that the changes that take place in the cerebral cortex, due to oxidative and/or metabolic stress, chronic pain, aging and/or trauma disturb the operation of normal cerebral cortical circuitry through the resulting degradation of synaptic function and neuronal and/or glial loss and degradation. The broad spectrum of changes that occur with systemic alterations in cerebral cortical function can be found in a wider array of neocortical regions including the somatosensory cortex.

The methods described below have been designed with the principle hypothesis that systemic alterations in cerebral cortical circuitry lead to changes in certain aspects of sensory perception. As it is believed that infarcts or stresses on the central nervous system (CNS) lead to changes in overall astrocytic activity and/or the status of the NMDA receptor system, the methods that will be predominantly used will be those based on results from neurophysiological experiments that demonstrated the conditions in which those systems are most sensitive. Recent work has elucidated the often underestimated connection between human perception of tactile stimulation with the dynamic cortical interactions that are evoked in the somatosensory cortex. Several of these studies have shown that performance on psychophysical tasks can provide quantitative measures that strongly correlate with, and thus could possibly be used to assess, cortical function.

In each of the following sections, the neurophysiological basis for the design of the human psychophysical experiment is described as well as the results obtained from such experiments. It should be noted that the sensory tests described herein are very different from the majority of prior art sensory tests for a number of reasons. The current tests can be administered with supra-threshold stimuli (rather than near-threshold), at dual skin sites (rather than single sites) and perhaps most importantly, can be targeted at maximizing cortical-cortical interactions (rather than minimizing them). The tests described are exemplary of both the sensory testing methods that can be used as well as the approach that will be used to develop additional sensory testing methods.

Figure 4:
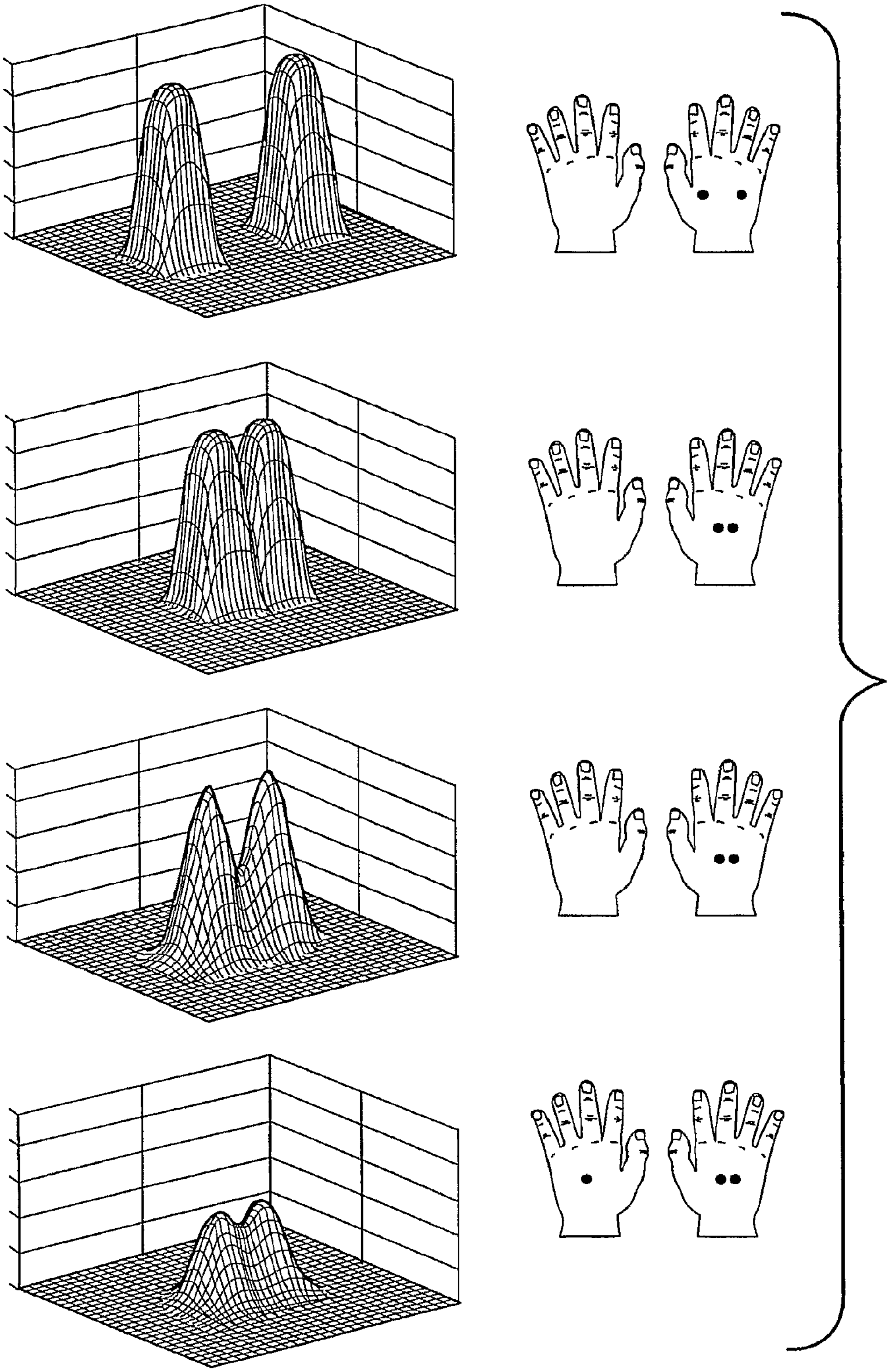
FIG. 4 is a top plan view of various hands showing various contact points at which stimulators according to the present subject matter can be used in different testing conditions along with corresponding graphs of brain activity.

FIG. 4 illustrates a model of predicted primary somatosensory cortex (SI) activity in response to specific conditions of tactile stimulation. When stimuli consisting of two points are oscillated on the skin at low-frequency 25 Hz flutter at distant sites, the peaks of SI response are distinct and non-overlapping, and therefore the subject is easily able to discriminate between the two points (see FIG. 4 top case). As the points are positioned at stimulus sites that are closer together, the peaks begin to overlap. Because the peaks are no longer easily distinguishable, discriminability is reduced (see FIG. 4, second case). Adding a same-site high-frequency 200 Hz vibration to the flutter stimuli ("complex" stimuli) has been shown to reduce the spatial extent of the peaks of response in SI and would make it easier to distinguish between two points on the skin (see FIG. 4, third case). Presentation of a stimulus at the same skin site on the unattended hand would reduce the magnitude of SI response by flutter stimulation. This reduction in magnitude of SI response would consequently lead to a reduction in the clarity (or contrast) between the activity evoked by the adjacent, or near-adjacent, cortical regions activated by the two stimuli, and as a result, lead to a decrease in spatial acuity (see FIG. 4, bottom case).

Because of the lack of communication between cortical regions in subjects with sensory deficit disorders (e.g., autism), the modified stimuli cases (see FIG. 4, third and fourth cases) do not produce the same change in sensory perception as in control subjects. Accordingly, by measuring changes in sensory perception between applications of baseline and augmented stimuli, deviation from a normal response can be observed. In this way, neurological diseases, disorders, or disruptions can be identified.

Figure 5A:
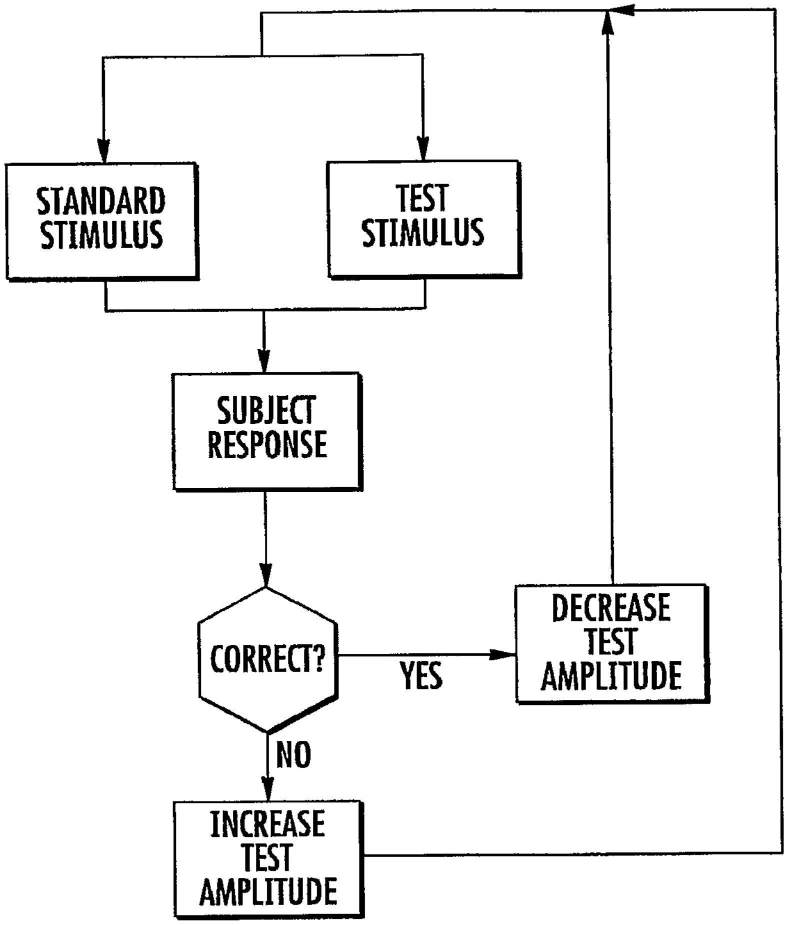
FIGS. 5A-5E are various block diagram flow charts of method steps possible in accordance with the present subject matter.

In one aspect, devices, systems, methods, and computer program products according to the present subject matter can be used for noninvasive screening of neurological disorders, wherein sets of simultaneous stimuli can be presented to the skin that differ only in the amplitude of the applied stimulus. As illustrated in FIG. 5A, a two-interval forced choice tracking paradigm can be used to compare a standard stimulus (e.g., 10 Hz flutter, 200 μm peak-to-peak—several orders of magnitude above threshold) with a test stimulus (e.g., initial amplitude at 205 μm). Both stimuli can be delivered simultaneously to the glabrous surface of two digit tips and the subject can be queried as to which stimulus is larger. The test subject can be queried as to which of the simultaneously delivered stimuli is larger. The amplitude of the test stimulus can be decreased with correct responses (e.g., 2 correct responses) and increased with incorrect response (e.g., one incorrect response).

The positions of the standard and test stimuli can be varied randomly. Both stimuli can be delivered for a predefined period of time (e.g., 0.5 seconds) with an inter-trial interval between applications of a stimulus (e.g., 5 seconds). Results can be obtained from a number of sessions (e.g., 10 sessions). Each session can consist of conditional runs, at least one in which the test and standard stimuli can be delivered out-of-phase, and at least another in which the stimuli can be delivered in-phase. In the out-of-phase condition, the starting phase of the sinusoid is randomly varied in order to prevent bias towards either the standard or the test stimulus.

On average, a subject is able to accurately discriminate between amplitudes of 220.9 vs. 200 μm under the condition of in-phase stimulation and 210.5 vs. 200 μm with out-of-phase stimulation. It is believed that this nearly two-fold difference in discrimination ability is accounted for by cortical mechanisms that maximize the contrast between the activity evoked in adjacent and near-adjacent cortical columns. Additionally, it is thought that the enhanced contrast of the out-of-phase condition is brought about by the exaggerated difference of the stimulus condition when the test stimulus is "on" (indent part of cycle) and the standard stimulus is "off".

Thus, the cortex seems to be most interested in detecting and storing the largest differences between the two stimuli. Although a large body of work has demonstrated that differences in the perceived intensity of a stimulus can be accounted for by the magnitude of the evoked population response and/or the firing rate, performance of this method is based on the observation that timing differences in stimuli that evoke responses in adjacent and/or near-adjacent cortical columns can manifest themselves in detecting a percept that is most often associated with the magnitude of the cortical response.

As noted above, because it is observed that subjects having some form of cortical diseases, disorders, or disruptions do not interpret complex stimuli the same way as the average subject due to failures in cortical-cortical interaction, an analysis of the test outcomes can be used to diagnose such diseases, disorders, or disruptions. In this regard, after the in-phase stimulation runs and out-of-phase stimulation runs are completed, the two sets of data can be compared. The level of disparity between the ability to discriminate stimulus amplitudes in the two conditions (or lack thereof) can thus be compared to known relationships between such results. In this way, the degree of functional connectivity between cortical areas can be objectively measurable.

Although this method (as well as those embodiments that follow) describes differences between healthy controls and subjects with a neurodevelopmental disorder, it is noted that similar sensory tracking can be effective in detecting the onset of neurodegenerative disorders that afflict similar mechanisms.

Similarly, varying the frequency of the test stimulus rather than the amplitude can improve the two-point threshold in subjects exhibiting normal cortical-cortical interaction. The reason this is significant is that it shows that a second pathway (mediated through the addition of the high frequency stimulus) improves sensory performance. With the neurologically abnormal subject (e.g., autism subject), there is little or no difference in this metric.

Figure 5B:
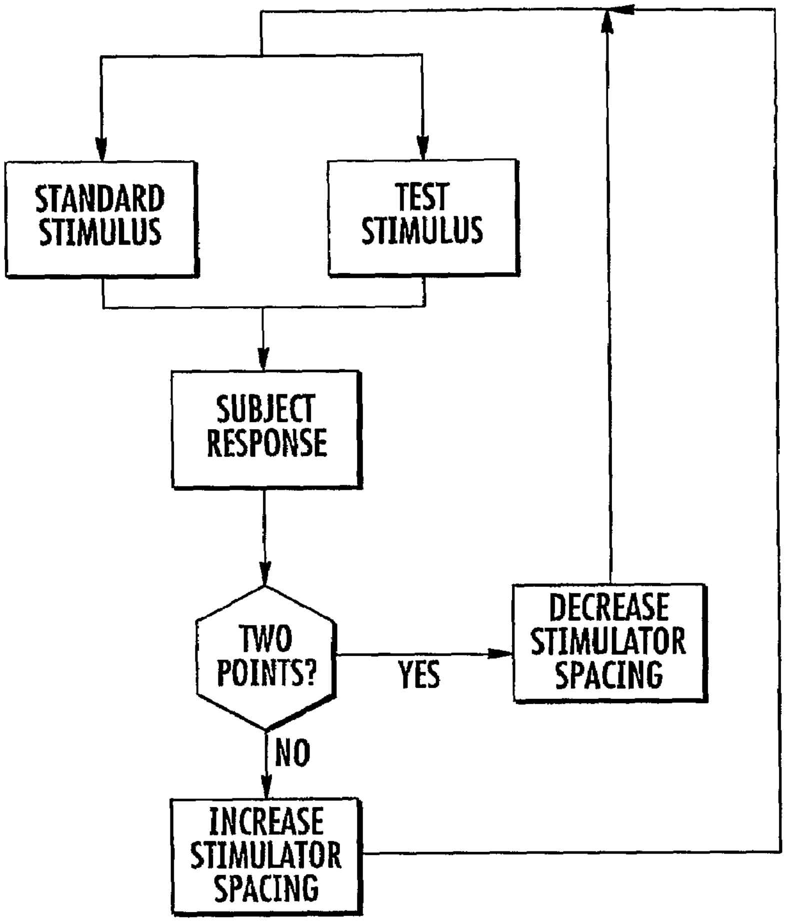

In this variation on the embodiment of the method described above, stimulus-dependent effects can be observed on two-point tracking of a flutter stimulus at the dorsal surface of the attended hand. As illustrated in FIG. 5B, a standard stimulus and a test stimulus having an equivalent frequency can be applied simultaneously at a defined spacing. The test subject can then be queried as to whether two points or only a single point are perceived. If both points are perceived, the spacing can be reduced; if both points are not perceived, the spacing can be increased. In this way, the test subject's two-point threshold can be identified.

The test can be repeated with a "complex" stimulus that is computational composite of a relatively low frequency (e.g., 25 Hz) and a relatively higher frequency (e.g., 200 Hz). It has been found according to the present subject matter that the two-point limen is reduced (spatial acuity is improved) with a complex stimulus of this kind. Specifically, in subjects exhibiting normal cortical communication, it is found that adding vibration to the unilateral two-point flutter stimulus improved spatial acuity by 20 to 25%. This improvement is not found (or is found to a lesser degree) in test subjects with impaired cortical communication.

Accordingly, as with the method above, once the two series of tests are completed, the two sets of data can be compared. The level of disparity between the two-point discrimination thresholds (or lack thereof) can be compared to known relationships between such results. In this way, the degree of functional connectivity between cortical areas can be objectively measurable.

In another embodiment, devices, systems, methods, and computer program products are provided for noninvasive screening of neurological disorders wherein bilateral stimuli (those delivered to both hands simultaneously) are added to a two-point spatial localization test, and the result of that addition is tracked.

Bilateral stimuli are processed very differently from unilateral stimuli, likely the result of interactions that occur between primary somatosensory cortex (SI) and secondary somatosensory cortex (SII) (these interactions take place both within the same hemisphere and between hemispheres). From animal studies, it has been found according to the present subject matter that the SI activation evoked by a contralateral flutter stimulus decreased when an ipsilateral stimulus is applied simultaneously to a mirror symmetric skin site. This observation leads to the prediction that some aspect of perceptual ability that is attributable to SI information processing—such as tactile spatial acuity—would suffer during the delivery of ipsilateral skin stimulation.

Figure 5C:
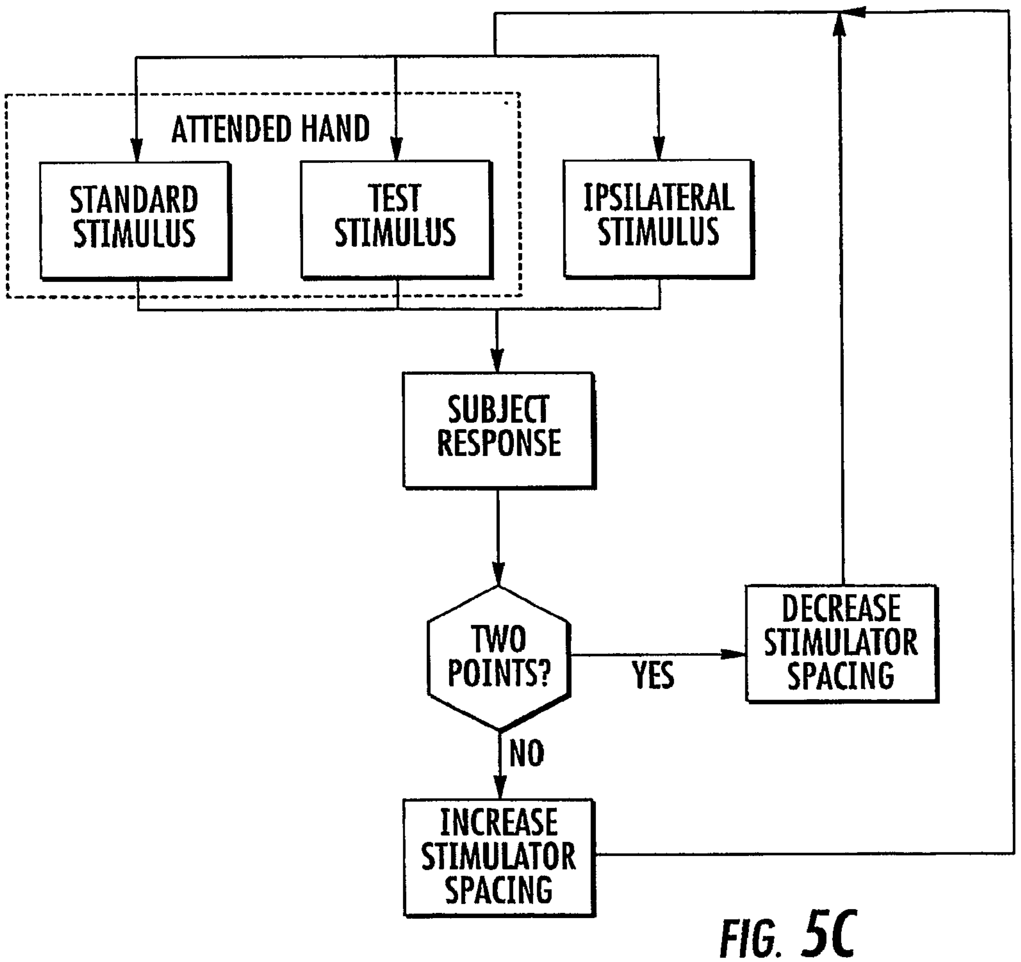

Accordingly, a method of this embodiment can involve evaluation of two point discriminative (TPD) capacity under stimulus conditions corresponding to those used in previous animal studies. As illustrated in FIG. 5C, two point limen tracking can be used to evaluate TPD in the presence of a simultaneous ipsilateral skin stimulus (i.e., tracking is performed on an "attended hand" (AH) while a second stimulus can be delivered simultaneously to the "unattended hand" (UH)).

It has been found according to the present subject matter that a control subject's tactile spatial acuity is worsened by 20% with 25 Hz flutter and by 30% with 200 Hz vibratory stimulation of the corresponding site on the opposite hand. These findings are regarded as perceptual correlates of the results obtained in imaging studies of SI in squirrel monkeys. In contrast, because some features of autism are thought to be attributable to defective interactions between the areas that comprise cerebral cortex, it is believed that the subjects with such disorders exhibit non-normal interactions that take place between SI and SII believed to be necessary for normal perception to occur. Specifically, there is no significant difference in the ability of the autistic subject to track two-point data when a second stimulus is delivered to the unattended hand as there is in the normal subject, most likely because of aberrant callosal connections (the connections running between the two hemispheres).

Accordingly, as with the preceding methods, once the two series of tests are completed, the two sets of data can be compared. The level of disparity between the two-point discrimination thresholds (or lack thereof) in the presence of stimulation of the unattended hand and in the absence of such ipsilateral stimulation can be compared to known relationships between such results. In this way, the degree of functional connectivity between cortical areas can be objectively measurable.

Figure 5D:
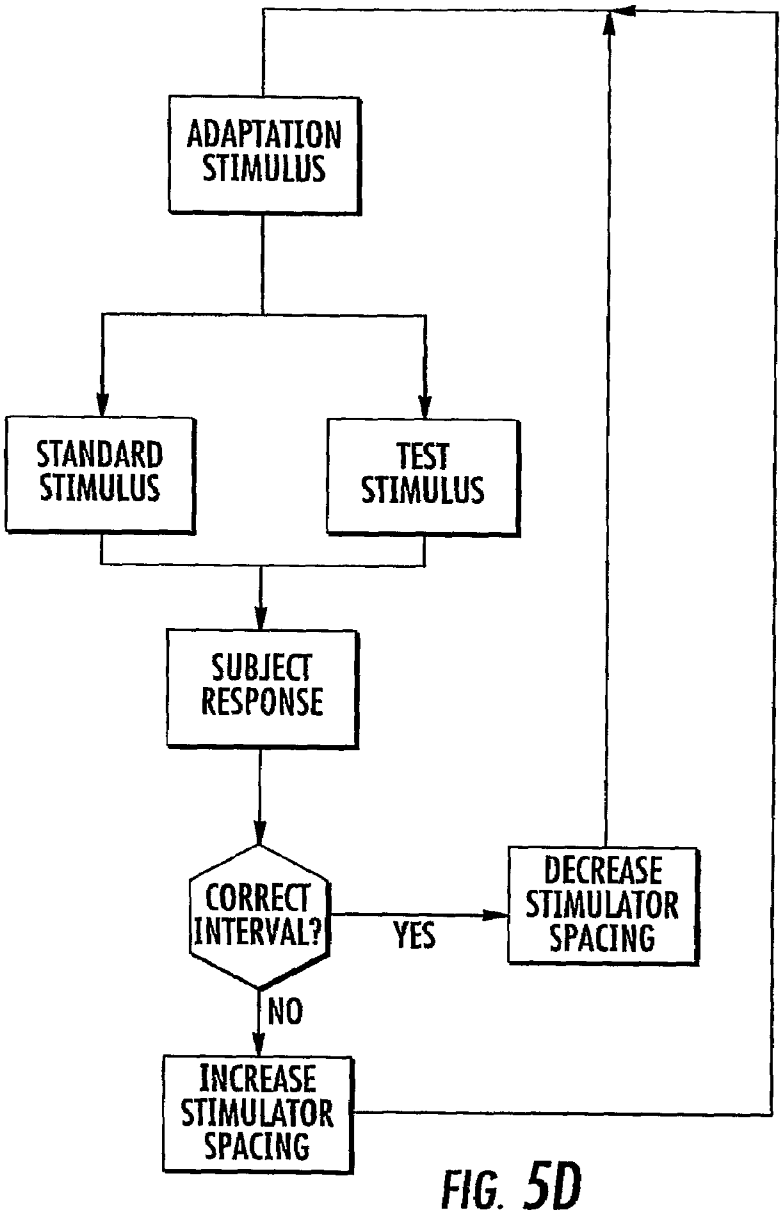

In yet another embodiment, devices, systems, methods, and computer program products are provided for noninvasive screening of neurological disorders wherein a two-interval forced-choice (2IFC) tracking protocol can be used to evaluate spatial localization. The subject is instructed to attend to the percept evoked by a vibrotactile stimulus (e.g., 25 Hz, 100 micron peak-to-peak amplitude). As illustrated in FIG. 5D, each trial can consist of three stimuli: 1) an adapting stimulus (e.g., either 5 or 0.5 sec in duration), 2) a standard stimulus (e.g., 0.5 sec) delivered at the same site as the adapting stimulus, and 3) a test stimulus (e.g., 0.5 sec) delivered to a skin site different from the standard stimulus. Unlike previous embodiments, the standard stimulus and test stimulus do not need to be applied simultaneously. Duration of the inter-stimulus (ISI) and inter-trial (ITI) intervals can be held constant for all runs (e.g., 2 and 30 sec, respectively). All stimuli can be superimposed on a pedestal of skin indentation (e.g., 500 μm), and following each stimulus the probe can be retracted to a position above the skin surface (e.g., 500 μm).

In each trial, the adapting stimulus can be delivered at a randomly selected locus (e.g., within the 20 mm array). The distance between the standard and test stimuli (e.g., 10 mm in the 1st trial at the start of each run) can be determined on the basis of subject performance. The subject can be instructed to report the interval during which the test stimulus is perceived to have occurred at the same skin site contacted by the adapting stimulus. If the subject chooses the correct interval, the distance between the skin sites contacted by the test and standard stimulus can be reduced (e.g., by 1 mm). If the incorrect interval is chosen, the distance can be increased (e.g., by 1 mm). This procedure can be repeated for a minimum number of trials (e.g., 20) in an attempt to identify the minimally detectable separation (spatial localization threshold) between the test and standard stimuli under a given adaptation condition (e.g., 5 sec vs. 0.5 sec). The order of the two adapting stimulus conditions (e.g., 5 or 0.5 sec) within a session can be randomized. Each subject can complete a number of sessions (e.g., 10), where each can consist of two runs.

For this method, sinusoidal vertical skin displacement stimuli can be delivered to the dorsum of the hand. A single stimulator (e.g., 2 mm diameter) can be positioned along a linear axis (e.g., 20 mm long) at incremental steps (e.g., 1 mm steps, step error of approximately 1%). The stimulator can be mounted on an adjustable mechanical arm with lockable joints that can be attached to a freestanding, rigid platform that enables convenient adjustment and maintenance of stimulus position.

Spatial discrimination tasks generate similar psychometric functions at the fingertip and the hand dorsum, differing essentially only by an order of magnitude. A transversally oriented linear array (20 mm in length) on the hand dorsum can be selected to receive the stimulation because: 1) innervation density across this skin region remains relatively constant; 2) the surface is easily accessible and permits convenient stimulator placement; 3) the surface is relatively flat, reducing confounds of skin curvature present at other potential sites of stimulation; and 4) it permits positioning of the subject's arm and hand in a comfortable and stable position for the full duration of an experimental session.

To eliminate potential confounding variables, it is possible—although not required—to configure the test to include provisions to account for various sensory biases. To ensure the comfort of the subject, and thereby help to minimize movement, the subject can be seated in a chair with the right arm placed resting on an X-ray bag filled with glass beads. The bag can be molded to fit the contours of the subject's arm, and when the subject is comfortable and the arm positioned to allow unimpeded access of the stimulator to the center of the dorsal surface of the right hand, the bag can be made rigid by evacuating it of air (e.g., by connecting the bag to a vacuum line). To help eliminate external sensory bias, the subject is unable to see either the experimenter or the stimulator and stimulus-control instrumentation. Further, white noise presented via headphones eliminates potential auditory cues.

For subjects having normal cortical connectivity (i.e., control subjects), an adaptation period (e.g., 5 seconds) generally results in a nearly two-fold improvement in spatial discrimination over that achieved with a 0.5 second adaptation period. For individuals having abnormal cortical connectivity, such as those with autism, adaptation or conditioning does not have an effect on the ability of the subject to spatially localize a stimulus.

Again, therefore, once tests are completed both with the inclusion of an adaptation stimulus and without an adaptation stimulus, the two sets of data can be compared. The level of disparity between the two-point discrimination thresholds (or lack thereof) in the presence of adaptation stimulation and in the absence of such conditioning stimulation can be compared to known relationships between such results. In this way, the degree of functional connectivity between cortical areas can be objectively measurable.

In still another embodiment, devices, systems, methods, and computer program products are provided for noninvasive screening of neurological disorders, wherein Temporal Order Judgment testing (TOJ), or the ability to determine the temporal order of two stimuli sequentially delivered to the skin, can be used to identify certain other neurological injuries or disorders. TOJ is typically on the order of 20-40 ms for healthy individuals, however, subjects diagnosed with dystonia, dyslexia, Parkinson's and TBI have all been shown to have TOJ measures at nearly two-fold that found for controls. It is suggested that these differences point to a degradation in the performance of the basal ganglia and/or cerebellum. Although most of the TOJ measures reported in current literature take between 30-120 minutes to obtain per subject, the method disclosed herein takes approximately 2-3 minutes. Additionally, the information is obtained about not only a subject's ability to assess temporal order, but a subject's ability to spatially and temporally integrate information from two sequentially delivered stimuli.

It has been found according to the present subject matter that when a carrier frequency is added to the applied stimuli (e.g., 25 Hz as background noise; background at 100 microns, stimulus pulse at 1000 microns), there is a pronounced decrease in a subject's ability to determine the temporal order of the two stimuli delivered. It is noted that delivering a higher frequency background stimulus (e.g., 200 Hz) at the same intensity does not produce comparable results. It is thought that this difference exists because of the differences in cortical organization that result from low (25 Hz) vs. high (200 Hz) frequency stimulation. The more organized response evoked by the 25 Hz stimulus results in a worse performance in the TOJ measure.

Synchronization of the cortical ensembles responding to the simultaneous digit tip stimulation at a lower frequency (e.g., 25 Hz) makes it difficult to discriminate between the two sites. This measure, since it is a simple indirect measure of synchronization, can be important in assessing an important facet of cerebral cortical health. In particular, if the NMDA receptor system is compromised, the impact that synchronization will have on CNS system response will be reduced. Synchronization of cortical ensembles is a well documented feature of the CNS, but it is difficult to quickly and quantitatively characterize.

Figure 5E:
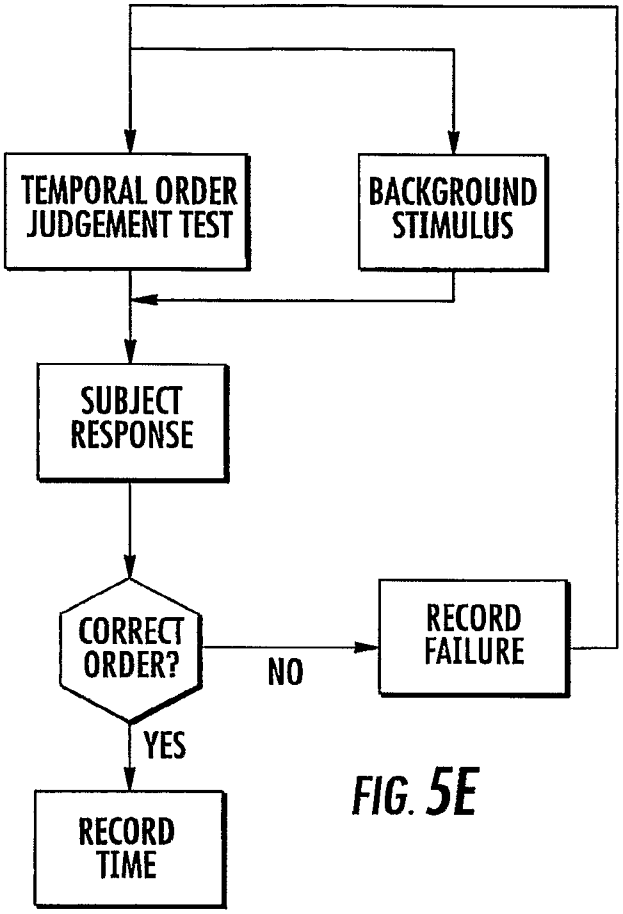

Accordingly, as illustrated in FIG. 5E, the method of this embodiment can involve the performance of a temporal order judgment test on the test subject. Two series of such tests can be performed, at least one in which a background stimulus can be added to the applied stimuli, and at least another in which no such background stimulus can be present. Once the series of tests are completed, the two sets of data can be compared. The level of disparity between the time of temporal order judgment (or failure to identify order) in the presence of a low frequency stimulus and in the absence of such additional stimulation can be compared to known relationships between such results. In this way, the degree of functional connectivity between cortical areas can be objectively measurable. For example, in subjects with autism, there is no degradation in performance with this added stimulus because of their lack of normal functional connectivity.

It will be understood that various details of the presently disclosed subject matter may be changed without departing from the scope of the presently disclosed subject matter. Furthermore, the foregoing description is for the purpose of illustration only, and not for the purpose of limitation.

Experimental Results

Figure 6A:
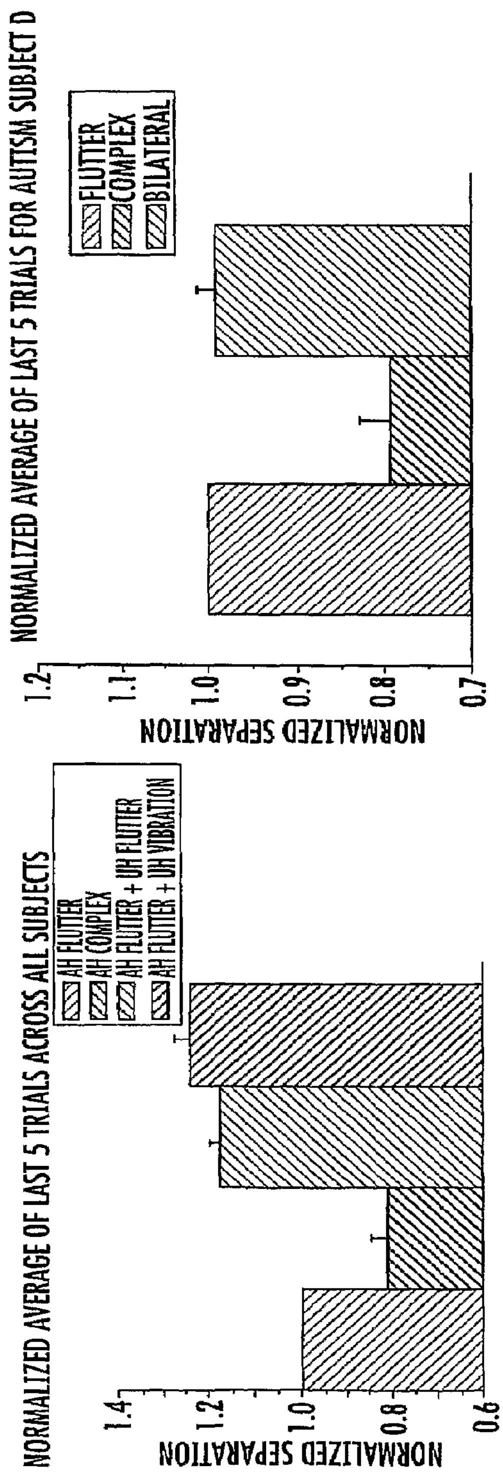
FIG. 6A illustrates the differences in responses between control subjects and subjects with autism following the application of complex and bilateral stimuli.
Figure 6B:
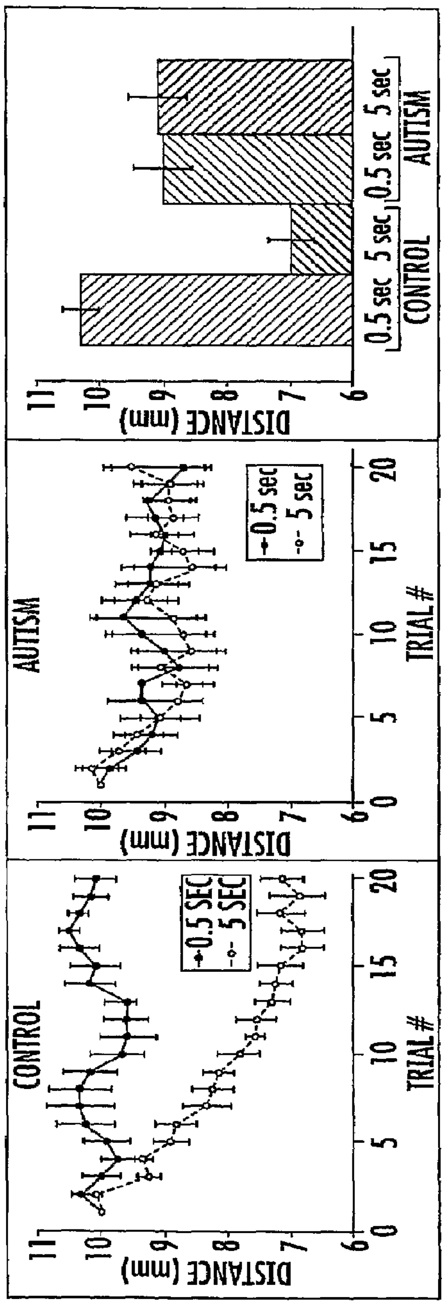
FIG. 6B illustrates the differences in responses between control subjects and subjects with autism following the application of an adaptation stimulus prior to spatial localization testing.

FIGS. 6A and 6B provide a sample of the results of experimental testing of the differences between healthy individuals and those exhibiting neurological diseases, disorders, or disruptions in their responses to somatosensory stimulation.

FIG. 6A illustrates the differences in responses between control subjects and subjects with autism following the application of complex and bilateral stimuli as describe hereinabove. Specifically, human psychophysical studies were performed to evaluate two point discriminative (TPD) capacity under stimulus conditions corresponding to those used in our animal studies. Two point limen tracking was used to evaluate TPD in the presence and absence of a simultaneous ipsilateral skin stimulus (i.e., tracking was performed on an "attended hand" (AH) while a second stimulus was delivered simultaneously to the "unattended hand" (UH)). The data showed clearly that each subject's tactile spatial acuity worsened by 20% with 25 Hz flutter and by 30% with 200 Hz vibratory stimulation of the corresponding site on the opposite hand (figure at left). These findings are regarded as perceptual correlates of the results obtained in our OIS imaging studies of SI in squirrel monkeys where it was found that bilateral stimuli evoked a stimulus that was approximately 30% smaller than contralateral stimuli. In contrast, preliminary data with subjects with autism found no reduction in spatial acuity with stimulation to the unattended hand suggesting (as others have) that the callosal projections between the two hemispheres is not functionally the same in subjects with autism as it is in control subjects.

FIG. 6B illustrates the differences in responses between control subjects and subjects with autism following the application of an adaptation stimulus prior to spatial localization testing as describe hereinabove. A two-interval forced choice tracking procedure was used to evaluate the effects of a 5 second pre-exposure to 25 Hz (100 μm peak-to-peak amplitude) adapting stimulation on a human subject's capacity to spatially localize a 25 Hz test stimulus. Adapting stimuli (either 0.5 or 5 seconds in duration) were presented at a randomized position within a 20 mm linear array oriented from radial to ulnar on the dorsum of the hand. Pairs of stimuli delivered subsequent to the adapting stimulus (standard and test comparison) were applied to the same location as the adapting stimulus (the "standard" stimulus) or to a different location (the "test" stimulus). Subjects were then questioned as to which of the 2 stimuli were located in the same position as the adapting stimulus. If the subject was correct, the distance between the location of the standard and test stimulus was reduced. In all cases, the 5 second adaptation period resulted in a nearly 2-fold improvement in spatial discrimination over that achieved with a 0.5 second adaptation period. FIG. 6B (top panels) shows the averaged data, across all subjects (n=4, 10 sessions per subject) for tracking the ability of a control subject to spatially differentiate two skin points contacted by the standard and test stimuli (presented non-simultaneously) for the two different adapting stimulus durations. However, the graphs at the bottom shows the results from the same protocol applied to autistic subjects (n=4). Thus, data that we have collected at this stage in the study suggest that adaptation or conditioning does not have an effect on the ability of the autistic subject to spatially localize a stimulus. It should be noted that although we have obtained what could be regarded as significant findings, we have done so with a limited exposure to the subject population in question (less than 1½ hours of sensory testing). Each of the testing sessions, for both controls and autistics, takes on the order of 5-10 minutes.

What is claimed is:

1. A method of screening for a neurological disorder, comprising:

(a) providing a portable, vibrotactile stimulation device comprising:

(i) a plurality of stimulators for providing vibrotactile stimulation;

(ii) stimulation drivers for driving the stimulators; and (iii) whereby the stimulators are independently controllable and operable for controlled stimulation of a subject with independently controllable stimulation parameters;

(b) providing vibrotactile stimulation to the subject, wherein the vibrotactile stimulation comprises a standard independently controllable stimulation parameter and a test independently controllable stimulation parameter;

(c) querying the subject for the subject's response to the standard and test stimulation parameters and recording and generating a tracking report based upon the response information;

(d) repeating steps (b) and (c), wherein the test stimulation parameter is decreased for a correct subject response and increased for an incorrect subject response such that the subject's discrimination ability is determined;

(e) repeating steps (b)-(d) in the presence of a modified independently controllable stimulation parameter that is provided to the subject such that the subject's discrimination ability is determined in the presence of the modified stimulation parameter; and (f) comparing the subject's discrimination ability in the presence and absence of the modified stimulation parameter, wherein a lack of a change in discrimination ability in the presence of the modified stimulation parameter indicates a neurological-disorder.

2. The method of claim 1, wherein the independently controllable stimulation parameter comprises one or more of:

(a) amplitude;

(b) frequency;

(c) phase relationship;

(d) onset time;

(e) duration;

(f) vertical displacement;

(g) lateral displacement; or (h) force offset.

3. The method of claim 1, wherein the vibrotactile stimulation of step (b) is provided to one of the subject's hands.

4. The method of claim 1, wherein the modified independently controllable stimulation parameter consists of delivery of a simultaneous independently controllable stimulation parameter to the corresponding site of the opposite hand of the subject.

5. The method of claim 1, wherein the modified independently controllable stimulation parameter consists of delivery to the subject of an adaptation independently controllable stimulation parameter prior to step (b).

6. The screening method of claim 1, wherein the modified stimulation parameter consists of addition of a same site high frequency or high amplitude vibration to the test stimulation parameter.

7. The screening method of claim 6, wherein the same site high frequency vibration is a 200 Hz vibration.

8. The screening method of claim 1, wherein the query to the subject is to which of the stimulation parameters are larger, wherein the decrease for a correct subject response and the increase for an incorrect response is in an amplitude or a frequency of the test stimulation parameter, and wherein the modified stimulation parameter is a delivery to the subject of a simultaneous bilateral, contralateral, or ipsilateral stimulation parameter, a delivery of a simultaneous stimulation parameter to the corresponding site of the opposite hand of the subject, or a delivery to the subject of an adaptation independently controllable stimulation parameter prior to step (b).

9. The screening method of claim 1, wherein the standard stimulation parameter and the test stimulation parameter are applied simultaneously at a low-frequency flutter vibration to evaluate the subject's two point discriminative capacity, wherein the decrease in the test stimulation parameter in response to the correct subject response is a decrease in the distance on the subject's skin between the standard and the test stimulation parameters until the subject is no longer able to discriminate between the two stimulation parameters and senses only a single stimulation parameter, and wherein the modified stimulation parameter is addition of a same site high frequency or high amplitude vibration to the test stimulation parameter, a delivery of a simultaneous bilateral, contralateral, or ipsilateral tactile stimulation parameter to the subject, or a delivery of a simultaneous independently controllable stimulation parameter to the corresponding site of the opposite hand of the subject.

10. The screening method of claim 9, wherein the modified stimulation parameter is the addition of the same site high frequency or high amplitude vibration to the test stimulation parameter and wherein the lack of a change in discrimination ability in the presence of the modified stimulation parameter is a lack of a decrease in two point discriminative capacity.

11. The screening method of claim 9, wherein the modified stimulation parameter is the delivery of a simultaneous stimulation parameter to the corresponding site of the opposite hand of the subject and wherein the lack of a change in discrimination ability in the presence of the modified stimulation parameter is a lack of a decrease in two point discriminative capacity.

12. The screening method of claim 9, wherein the low-frequency flutter vibration is a 25 Hz flutter.

13. The screening method of claim 1, wherein the modified stimulation parameter consists of providing to the subject a simultaneous bilateral, contralateral, or ipsilateral independently controllable stimulation parameter.

14. The method of claim 1, wherein the standard stimulation parameter and the test stimulation parameter are applied simultaneously, wherein the query to the subject is to which of the stimulation parameters are larger, wherein the decrease for a correct subject response and the increase for an incorrect response is in an amplitude or a frequency of the test stimulation parameter, wherein the modified stimulation parameter is a delivery of the test and the standard stimulation parameters at least once under an in-phase condition to determine the subject's discrimination ability and at least once under an out-of-phase condition to determine the subject's discrimination ability, and wherein the lack of change in discrimination ability is a lack of an improved out-of-phase discrimination ability.

15. The method of claim 1 wherein the neurological disorder comprises one of autism, schizophrenia, Alzheimer's disease, chronic pain, traumatic brain injury, migraine, attention deficit hyperactivity disorder, and combinations thereof.

16. The method of claim 1, wherein the standard stimulation parameter and the test stimulation parameter are delivered to evaluate the subject's two point discriminative capacity, wherein the decrease in the test stimulation parameter in response to the correct subject response is a decrease in the distance on the subject's skin between the standard and the test stimulation parameters until the subject is no longer able to discriminate between the two stimulation parameters and senses only a single stimulation parameter, and wherein the modified stimulation parameter is delivery to the subject of an adaptation independently controllable stimulation parameter prior to step (a) delivered to the same site as the standard stimulation parameter.

17. The method of claim 1, wherein the adaptation stimulation parameter is a 5 sec vibrotactile stimulus or a 0.5 sec vibrotactile stimulus.

18. A method of screening for a neurological disorder, comprising:

(a) providing a portable, vibrotactile stimulation device comprising:
  (i) a plurality of stimulators for providing vibrotactile stimulation;
  (ii) stimulation drivers for driving the stimulators; and
  (iii) whereby the stimulators are independently controllable and operable for controlled stimulation of a subject with independently controllable stimulation parameters;

(b) providing two sequential vibrotactile stimuli to the subject, wherein the sequential tactile stimuli are each an independently controllable stimulation parameter;

(c) querying the subject for a response in regard to the temporal order of the two stimulation parameters and recording and generating a tracking report based upon the response information;

(d) repeating steps (b) and (c), wherein a time between delivery of the sequential stimulation parameters is decreased for a correct subject response and increased for an incorrect subject response such that the subject's temporal order judgment is determined, wherein the subject's temporal order judgment is the subject's discrimination ability;

(e) repeating steps (b)-(d) in the presence of a modified independently controllable stimulation parameter, wherein the modified stimulation parameter is a low frequency background flutter, such that the subject's discrimination ability is determined in the presence of the low frequency background flutter; and (f) comparing the subject's discrimination ability in the presence and absence of the low frequency background flutter, wherein a lack of a change in discrimination ability in the presence of the low frequency background flutter indicates a neurological disorder.

19. The method of claim 18, wherein the independently controllable stimulation parameter comprises one or more of:

(a) amplitude;
(b) frequency;
(c) phase relationship; or
(d) force offset.

20. The method of claim 18, wherein the neurological disorder comprises one of autism, schizophrenia, Alzheimer's disease, chronic pain, traumatic brain injury, migraine, attention deficit hyperactivity disorder, and combinations thereof.

21. The method of claim 18, wherein the stimulation parameters are delivered to the subject's hand(s).

22. The method of claim 21, wherein the stimulation parameters are delivered to a glabrous surface of the digits of the subject's hand or a dorsum of the subject's hand.

* * * * *